(12) United States Patent
Tornier et al.

(10) Patent No.: US 9,814,592 B2
(45) Date of Patent: Nov. 14, 2017

(54) SILICONE NUCLEUS IMPLANTS

(71) Applicant: CLARIANCE (S.A.S.), Dainville (FR)

(72) Inventors: Alain Tornier, Saint Ismier (FR); Guy Viart, Saint Leger (FR); Jean-Yves Leroy, Campagne les Hesdin (FR); Adrien Billon, Ronchin (FR)

(73) Assignee: CLARIANCE, Dainville (FR)

( * ) Notice: Subject to any disclaimer, the term of this patent is extended or adjusted under 35 U.S.C. 154(b) by 0 days.

(21) Appl. No.: 13/652,797

(22) Filed: Oct. 16, 2012

(65) Prior Publication Data

US 2013/0103155 A1  Apr. 25, 2013

Related U.S. Application Data

(60) Provisional application No. 61/549,328, filed on Oct. 20, 2011.

(51) Int. Cl.
*A61F 2/44* (2006.01)
*A61F 2/46* (2006.01)
*A61F 2/30* (2006.01)

(52) U.S. Cl.
CPC ............ *A61F 2/442* (2013.01); *A61F 2/4611* (2013.01); *A61F 2/4405* (2013.01); *A61F 2002/302* (2013.01); *A61F 2002/30563* (2013.01); *A61F 2002/30581* (2013.01); *A61F 2002/30677* (2013.01); *A61F 2002/444* (2013.01); *A61F 2210/0004* (2013.01); *A61F 2230/0065* (2013.01); *A61F 2230/0091* (2013.01)

(58) Field of Classification Search
CPC ............ A61F 2002/30583; A61F 2/44–2/447
USPC ........................................... 623/17.11–17.16
See application file for complete search history.

(56) References Cited

U.S. PATENT DOCUMENTS

| | | | |
|---|---|---|---|
| 2001/0049527 A1* | 12/2001 | Cragg | A61B 17/1671 606/279 |
| 2007/0038300 A1* | 2/2007 | Bao et al. | 623/17.12 |
| 2007/0150059 A1* | 6/2007 | Ruberte et al. | 623/17.12 |
| 2008/0172126 A1* | 7/2008 | Reynolds | A61B 17/8808 623/17.16 |
| 2008/0195210 A1* | 8/2008 | Milijasevic et al. | 623/17.16 |
| 2009/0254186 A1* | 10/2009 | Tornier et al. | 623/17.16 |
| 2010/0100184 A1* | 4/2010 | Krueger et al. | 623/17.12 |

FOREIGN PATENT DOCUMENTS

| | | |
|---|---|---|
| FR | 11/00199 | 9/1955 |
| WO | 2009/130417 | 10/2009 |

* cited by examiner

*Primary Examiner* — Jan Christopher Merene
*Assistant Examiner* — Steven Cotroneo
(74) *Attorney, Agent, or Firm* — Young & Thompson

(57) ABSTRACT

A nucleus implant includes a core (10) arranged inside a nucleus pulposus space (Es) obtained after nucleotomy of the intervertebral disk (Di) and at least one extension (11) penetrating inside at least one channel (Co) formed in the vertebral body of the corresponding vertebra (Va, Vb) to strengthen and ensure a connection between the nucleus implant (1) and the bone body of the vertebra (Va) and/or (Vb) through the diffusion or migration of the viscoelastic material making up the nucleus implant in the cancellous bone of the vertebra.

18 Claims, 3 Drawing Sheets

SILICONE NUCLEUS IMPLANTS

BACKGROUND OF THE INVENTION

Field of the Invention

The present invention relates to a silicone nucleus implant, arranged between a superjacent vertebra and an underlying vertebra of a spinal segment, constituting an intervertebral bracing device that absorbs shocks and ensures the mobility of the functional unit formed by said vertebrae.

Description of the Related Art

The deterioration of the nucleus is generally the first factor that leads to deterioration of the disk, and consequently of the joint facets. This deterioration can cause hernias, and this problem is often treated by nucleotomy.

However, although the pain disappears in immediate post-op, the loss of height of the disk and the hyper-mobility of the consecutive segment gradually accentuate the deterioration of the spinal segment, with pain reappearing and sometimes with deterioration of the adjacent stages.

Early nucleus replacement for such patients may be an effective alternative to total replacement of the disk or fusion of the segment.

In fact, maintaining a sufficient intervertebral height with quasi-normal mobility may impart a certain degree of stability to the segment, thereby slowing or even stopping deterioration phenomena.

Known from international patent application WO 2009/130417, belonging to the applicant, is a nucleus implant having at least one filling element having at least one continuous filament which is arranged inside a nucleus pulposus space obtained after nucleotomy of the intervertebral disk, and which follows a ring-shaped profile, and of which the stack of spirals delimits a central inner space that is filled with a product such as a gel or paste, a fiber-based product, or an injectable viscoelastic material.

It will be noted that this type of implant has problems with gradually migrating toward the medullary channel during repeated extension flexion movements of said vertebrae of the spinal segment, since the implant is not connected or attached to the body of the corresponding vertebrae.

SUMMARY OF THE INVENTION

The nucleus implant according to the present invention aims to improve the nucleus implant by reducing the number of components it includes and guaranteeing a stable and effective connection between the implant and the vertebral bodies of the concerned spinal segment.

The nucleus implant according to the present invention consists of a core arranged inside a nucleus pulposus space obtained after nucleotomy of the intervertebral disk and at least one extension penetrating inside at least one channel formed in the vertebral body of the corresponding vertebra to strengthen and ensure a connection between the nucleus implant and the bone body of the vertebra through the diffusion or migration of the viscoelastic material making up said nucleus implant in the cancellous bone.

The nucleus implant according to the present invention has a core comprising at least two extensions that extend on either side of the center of said core.

The nucleus implant according to the present invention has a core and extensions that are obtained from a fluid or organosiloxane-based paste composition, autopolymerizing at ambient temperature in permanently elastic silicone.

The nucleus implant according to the present invention has a core and extensions that are obtained from a polydimethylsiloxane-based composition.

The nucleus implant according to the present invention has a core and extensions that are obtained from a composition containing platinum catalyst.

The nucleus implant according to the present invention has a core and extensions that are obtained from a composition containing a catalyst with a base of hydride-functionalized siloxane and vinyl-functionalized siloxane.

BRIEF DESCRIPTION OF THE DRAWING FIGURES

The following description, done in reference to the appended drawings, provided as non-limiting examples, will make it possible to better understand the invention, the features thereof, and the advantages it may procure:

FIGS. 1 and 2 show a spinal segment Sr of a vertebral column whereof at least one of the superjacent Va and underlying Vb vertebrae will be pierced using a drilling device (not shown) with at least one bone channel having a curved profile Co so as to reach the upper surface of a damaged intervertebral disk Di.

Figure 1:
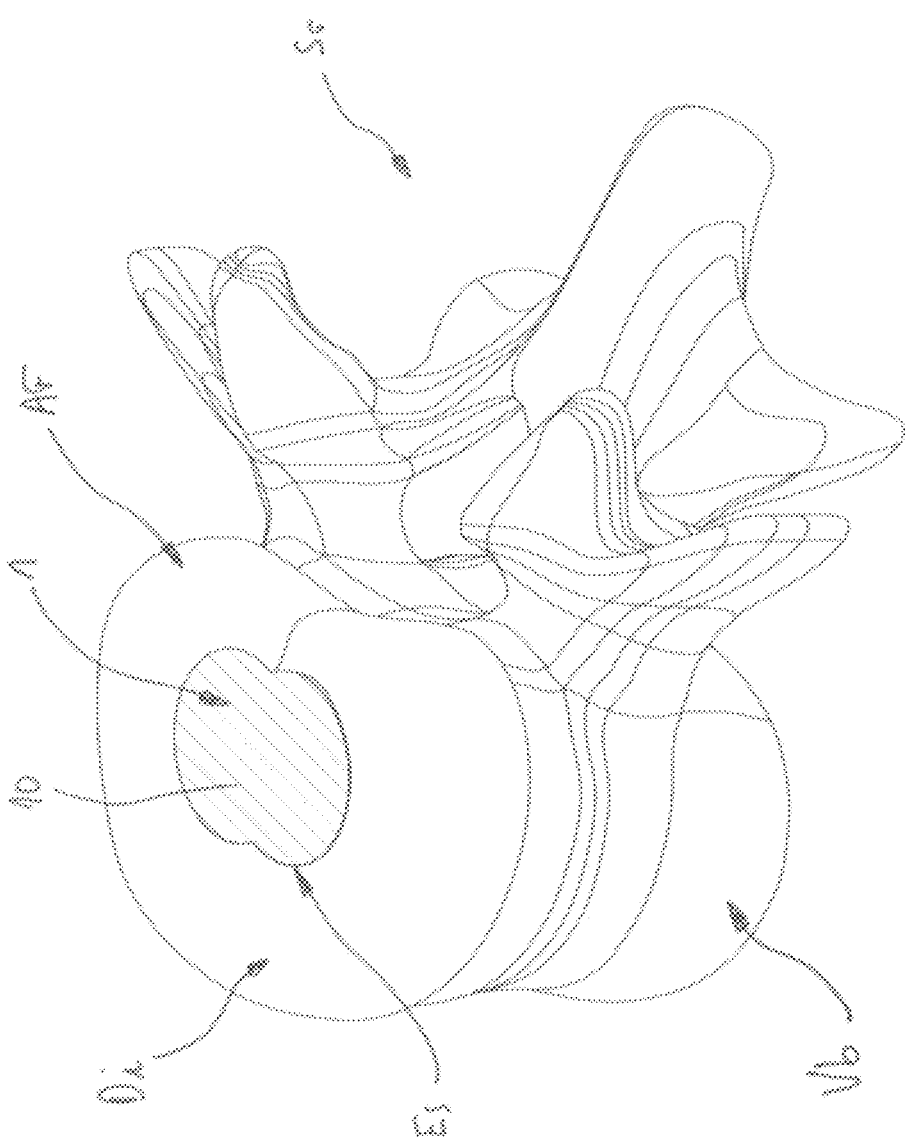
FIG. 1 is an exploded perspective view illustrating the nucleus implant according to the present invention, the core of which is obtained by injecting a silicone-based material.
Figure 2:
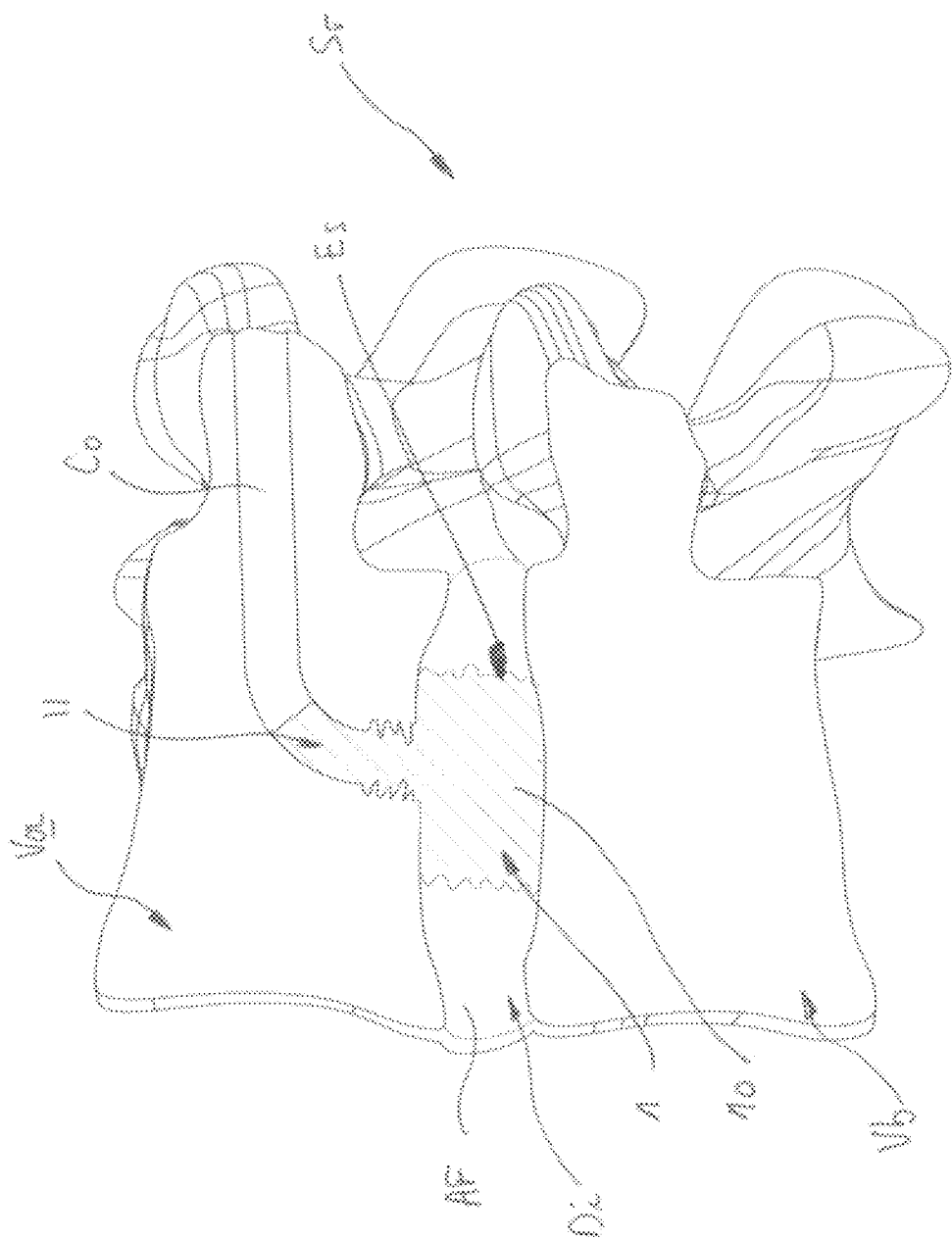
FIG. 2 is a cross-sectional view illustrating the nucleus implant according to the present invention, the core of which is obtained by injecting a silicone-based material.
Figure 3:
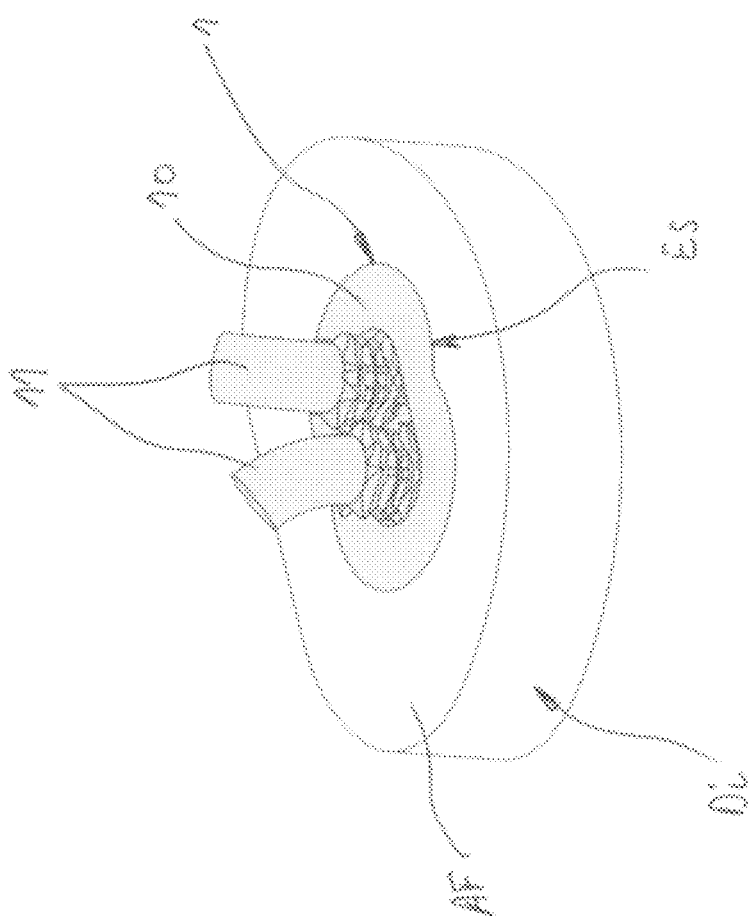
FIG. 3 is a perspective view diagrammatically illustrating the nucleus implant, the core of which for example has at least two cords extending on either side of the center of said core according to the present invention.

Drilling the superjacent vertebra Va with a curved profile, for example, makes it possible to use a transosseous percutaneous surgical approach to reach the nucleus of the intervertebral disk Di so as then to be able to perform the necessary operations on the damaged intervertebral disk until a nucleus pulposus space Es is obtained at the center of the "annulus fibrosis" AF.

DETAILED DESCRIPTION OF THE INVENTION

The drilling of the superjacent Va and/or underlying Vb vertebrae with a curved profile is for example done using a drilling device described and protected in patent application FR11/00199, belonging to the applicant.

When the bone channel with the curved profile Co is obtained, it allows the insertion, using an injection device (not shown), of a viscoelastic material that autopolymerizes at ambient temperature, making it possible to produce a nucleus implant 1 inside the nucleic pulposus space Es.

The nucleus implant 1 is made from silicone or a viscoelastic material that autopolymerizes at ambient temperature. The nucleus implant 1 is made up of a core 10 having at least one extension 11 penetrating inside the channel(s) with a curved profile Co formed in the vertebral body of the corresponding vertebra.

Each extension 11 extending from the core 10 makes it possible to provide a connection between said core and the bone body of the corresponding vertebra Va and/or Vb, preventing any possibility of the nucleus implant 1 migrating relative to the "annulus fibrosis" AF and said vertebrae.

Each extension 11 makes it possible to strengthen and ensure a connection between the nucleus implant 1 and the bone body of the vertebra Va/Vb through the diffusion or migration of the viscoelastic material that autopolymerizes at ambient temperature in the cancellous bone of said vertebral body of the corresponding vertebra Va, Vb.

In fact, the connection produced by the extensions 11 makes it possible to keep the nucleus implant 1 in place between the vertebrae Va and/or Vb and thereby prevents the gradual migration of the latter toward the medullary channel during repeated extension flexion movements of said vertebrae Va and/or Vb of the spinal segment Sr.

Each extension 11 of the nucleus implant 1 also makes it possible to obstruct the corresponding curved bone channel Co to prevent any possibility of foreign body migration inside the intervertebral disk Di.

The nucleus implant 1 made up of the core 10 and the extensions 11 can be obtained from a fluid or organosiloxane-based paste composition autopolymerizing at ambient temperature in permanently elastic silicone.

The nucleus implant 1 made up of the core 10 and extensions 11 is obtained from a fluid or organosiloxane-based paste composition of the polydimethylsiloxane type autopolymerizing at ambient temperature in permanently elastic silicone.

The nucleus implant 1 made up of the core 10 and extensions 11 is obtained from a fluid or organosiloxane-based paste composition that may be of the polydimethylsiloxane type autopolymerizing at ambient temperature in permanently elastic silicone and containing platinum catalyst.

The nucleus implant 1 made up of the core 10 and extensions 11 is obtained from a fluid or organosiloxane-based paste composition that may be of the polydimethylsiloxane type autopolymerizing at ambient temperature in permanently elastic silicone and containing a catalyst with a base of hydride-functionalized siloxane and vinyl-functionalized siloxane.

It must also be understood that the preceding description has been provided solely as an example and in no way limits the scope of the invention, and it would not go beyond the scope of the invention to replace the described details of the embodiments with any equivalent means.

The invention claimed is:

1. A nucleus implant configured to be arranged between a superjacent vertebra and an underlying vertebra of a spinal segment, constituting an intervertebral bracing device that absorbs shocks and ensures mobility of a functional unit formed by said vertebrae, comprising:
    a permanently elastic core configured to be arranged inside a nucleus pulposus space obtained after nucleotomy of an intervertebral disk; and
    two permanently elastic extensions arranged on a same face of the permanently elastic core, each extension having a curved cylindrical profile and configured to penetrate inside a corresponding curved cylindrical profile of at least one channel formed in a vertebral body of the corresponding vertebra to strengthen and ensure a connection between the nucleus implant and a bone body of the vertebra through diffusion or migration of viscoelastic material making up said nucleus implant in a cancellous bone of said vertebra, the at least one channel being a feed channel for a fluid or paste of an organosiloxane composition that forms permanently elastic silicone that comprises the permanently elastic core and the two permanently elastic extensions.

2. The nucleus implant according to claim 1, wherein the two extensions extend on either side of a center of said core.

3. The nucleus implant according to claim 2, wherein the fluid or paste organosiloxane composition autopolymerizes at ambient temperature.

4. The nucleus implant according to claim 3, wherein the core and extensions of said implant are obtained from a polydimethylsiloxane-based composition.

5. The nucleus implant according to claim 4, wherein the core and extensions of said implant are obtained from a composition containing platinum catalyst.

6. The nucleus implant according to claim 3, wherein the core and extensions of said implant are obtained from a composition containing platinum catalyst.

7. The nucleus implant according to claim 3, wherein the core and extensions of said implant are obtained from a composition containing a catalyst with a base of hydride-functionalized siloxane and vinyl-functionalized siloxane.

8. The nucleus implant according to claim 2, wherein the core and extensions of said implant are obtained from a composition containing a catalyst with a base of hydride-functionalized siloxane and vinyl-functionalized siloxane.

9. The nucleus implant according to claim 1, wherein the permanently elastic core has a generally figure-8 shape.

10. The nucleus implant according to claim 1, wherein each permanently elastic extension has a base from which congruencies extend.

11. A nucleus implant configured to be arranged between a superjacent vertebra and an underlying vertebra of a spinal segment, constituting an intervertebral bracing device that absorbs shocks and ensures mobility of a functional unit formed by said vertebrae, comprising:
    a permanently elastic core configured to be arranged inside a nucleus pulposus space obtained after nucleotomy of an intervertebral disk; and
    two permanently elastic extensions extending on either side of a center of a same face of the permanently elastic core, each extension having a curved cylindrical profile, each extension being configured to penetrate inside a corresponding curved cylindrical profile of at least one channel formed in a vertebral body of the corresponding vertebra to strengthen and ensure a connection between a nucleus implant and a bone body of the vertebra through diffusion or migration of viscoelastic material making up said nucleus implant in a cancellous bone of said vertebra, the at least one channel being a feed channel for a fluid or paste of a organosiloxane composition that autopolymerizes at ambient temperature to form permanently elastic silicone that comprises the permanently elastic core and the two permanently elastic extensions.

12. The nucleus implant according to claim 11, wherein the core and extensions of said implant are obtained from a polydimethylsiloxane-based composition.

13. The nucleus implant according to claim 11, wherein the core and extensions of said implant are obtained from a composition containing platinum catalyst.

14. The nucleus implant according to claim 11, wherein the permanently elastic core has a generally figure-8 shape.

15. The nucleus implant according to claim 11, wherein each permanently elastic extension has a base from which congruencies extend.

16. A nucleus implant configured to be arranged between a superjacent vertebra and an underlying vertebra of a spinal segment, constituting an intervertebral bracing device that absorbs shocks and ensures mobility of a functional unit formed by said vertebrae, comprising:

a permanently elastic core configured to be arranged inside a nucleus pulposus space obtained after nucleotomy of an intervertebral disk; and two permanently elastic extensions projecting from a same face of the permanently elastic core, each elastic extension having a curved cylindrical profile, each extension being configured to penetrate inside a corresponding curved cylindrical profile of at least one channel formed in a vertebral body of the corresponding vertebra to strengthen and ensure a connection between a nucleus implant and a bone body of the vertebra through diffusion or migration of viscoelastic material making up said nucleus implant in a cancellous bone of said vertebra, wherein the at least one channel is a feed channel so that the core and extensions of said implant are obtained from a fluid or polydimethylsiloxane paste composition containing platinum catalyst, autopolymerizing at ambient temperature in permanently elastic silicone.

17. The nucleus implant according to claim 16, wherein the permanently elastic core has a generally figure-8 shape.

18. The nucleus implant according to claim 16, wherein each permanently elastic extension has a base from which congruencies extend.

* * * * *